United States Patent
Kobayashi et al.

(10) Patent No.: US 10,922,812 B2
(45) Date of Patent: Feb. 16, 2021

(54) IMAGE PROCESSING APPARATUS, X-RAY DIAGNOSTIC APPARATUS, AND IMAGE PROCESSING METHOD

(71) Applicant: CANON MEDICAL SYSTEMS CORPORATION, Otawara (JP)

(72) Inventors: Yoshimasa Kobayashi, Nasushiobara (JP); Hisanori Kato, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 265 days.

(21) Appl. No.: 16/001,358

(22) Filed: Jun. 6, 2018

(65) Prior Publication Data
US 2018/0357762 A1  Dec. 13, 2018

(30) Foreign Application Priority Data

Jun. 12, 2017  (JP) .................... 2017-115419

(51) Int. Cl.
*G06T 7/00* (2017.01)
*G06T 7/60* (2017.01)
(Continued)

(52) U.S. Cl.
CPC ............ *G06T 7/0012* (2013.01); *A61B 6/025* (2013.01); *A61B 6/486* (2013.01); *A61B 6/505* (2013.01); *G06T 5/50* (2013.01); *G06T 7/60* (2013.01); *G06T 11/003* (2013.01); *G06T 11/008* (2013.01); *G06T 11/60* (2013.01); *G06T 15/005* (2013.01); *G06T 15/08* (2013.01); *G06T 2200/04* (2013.01); *G06T 2200/24* (2013.01); *G06T 2207/10112* (2013.01);
(Continued)

(58) Field of Classification Search
CPC ......... A61B 6/486; A61B 6/025; A61B 6/505; G06T 2200/04; G06T 15/08; G06T 5/50; G06T 7/60; G06T 2200/24; G06T 2207/20216; G06T 15/005; G06T 2207/30008; G06T 11/003; G06T 2207/10112; G06T 2207/20101; G06T 11/60; G06T 7/0012; G06T 2207/10116; G06T 11/008; G06T 2210/41
See application file for complete search history.

(56) References Cited

U.S. PATENT DOCUMENTS

2005/0105678 A1* 5/2005 Nakashima .......... A61B 6/4085
378/4
2016/0073986 A1* 3/2016 Saito .................... A61B 6/032
378/4
(Continued)

FOREIGN PATENT DOCUMENTS

JP  2009-232982  10/2009

*Primary Examiner* — Yon J Couso
(74) *Attorney, Agent, or Firm* — Oblon, McClelland, Maier & Neustadt, L.L.P.

(57) ABSTRACT

An image processing apparatus according to an embodiment has processing circuitry configured to acquire three-dimensional medical image data; set coordinates of at least two or more elements to evaluate an evaluation target represented by the three-dimensional medical image data, on images of different positioning slices of the three-dimensional medical image data; calculate a measured value for evaluating the evaluation target based on the coordinates; and control a display to display the measured value.

16 Claims, 14 Drawing Sheets

(51) Int. Cl.
*G06T 11/00* (2006.01)
*G06T 15/00* (2011.01)
*G06T 11/60* (2006.01)
*A61B 6/02* (2006.01)
*A61B 6/00* (2006.01)
*G06T 5/50* (2006.01)
*G06T 15/08* (2011.01)

(52) U.S. Cl.
CPC ............ *G06T 2207/10116* (2013.01); *G06T 2207/20101* (2013.01); *G06T 2207/20216* (2013.01); *G06T 2207/30008* (2013.01); *G06T 2210/41* (2013.01)

(56) References Cited

U.S. PATENT DOCUMENTS

| | | | | |
|---|---|---|---|---|
| 2016/0081645 | A1* | 3/2016 | Fukuda | A61B 6/502 |
| | | | | 378/4 |
| 2017/0281110 | A1* | 10/2017 | Mandelkern | A61B 6/469 |
| 2018/0070894 | A1* | 3/2018 | Osaki | A61B 6/488 |
| 2019/0197741 | A1* | 6/2019 | Nishii | G06T 19/00 |

* cited by examiner

FIRST SLICE

SECOND SLICE

SECOND SLICE

SECOND SLICE

SUPERIMPOSED IMAGE

FIRST SLICE

THIRD SLICE

FIRST SLICE

SECOND SLICE

IMAGE PROCESSING APPARATUS, X-RAY DIAGNOSTIC APPARATUS, AND IMAGE PROCESSING METHOD

CROSS-REFERENCE TO RELATED APPLICATIONS

This application is based upon and claims the benefit of priority from Japanese Patent Application No. 2017-115419, filed on Jun. 12, 2017; the entire contents of which are incorporated herein by reference.

FIELD

Embodiments of the present invention relate to an image processing apparatus, an X-ray diagnostic apparatus, and an image processing method.

BACKGROUND

An X-ray diagnostic apparatus which irradiates a subject with X-rays and detects the X-rays transmitted through the subject to thereby perform X-ray imaging is widely used in the medical field. One of imaging methods of the X-ray diagnostic apparatus is tomosynthesis imaging. The tomosynthesis imaging is an imaging method of performing X-ray imaging, using the X-ray diagnostic apparatus in which an X-ray tube bulb and an X-ray detector are placed opposite to each other, a plurality of times on a subject positioned between the X-ray tube bulb and the X-ray detector while moving the X-ray tube bulb and the X-ray detector. Performing image processing such as image reconstruction on a plurality of pieces of projection data obtained by the plurality of times of X-ray imaging generates three-dimensional medical image data including a region of interest of the subject.

The three-dimensional medical image data obtained by the tomosynthesis imaging includes information in a thickness direction because three-dimensional information is obtained, unlike conventional two-dimensional data. This enables interpretation of radiogram of a bone or a lesion which have been conventionally hard to see, leading to an advantage of making it easier to find abnormality in the bone or the lesion. Therefore, the tomosynthesis imaging using the X-ray diagnostic apparatus is now increasingly spread at a clinical site.

However, the visibility of the bone can be enhanced by imaging the bone such as the femoral head or the sacrum form the side by the tomosynthesis imaging, but the femoral head and the sacrum are drawn in images of different slices respectively, and therefore when the measured results are tried to be left as records, they cannot be drawn in one image like a conventional two-dimensional image. Therefore, there is a problem of a complicated work when the captured images are tried to be left as records.

Besides, on the bones such as the femoral head and the sacrum, measuring an angle between the bones and measuring the distance between the bones using various auxiliary images are performed as a part of a diagnosis of a pelvis distortion. Therefore, a method is desired which measures the angle and distance between the bones even from three-dimensional medical image data obtained by the tomosynthesis imaging without performing the complicated work.

DETAILED DESCRIPTION

Figure 1:
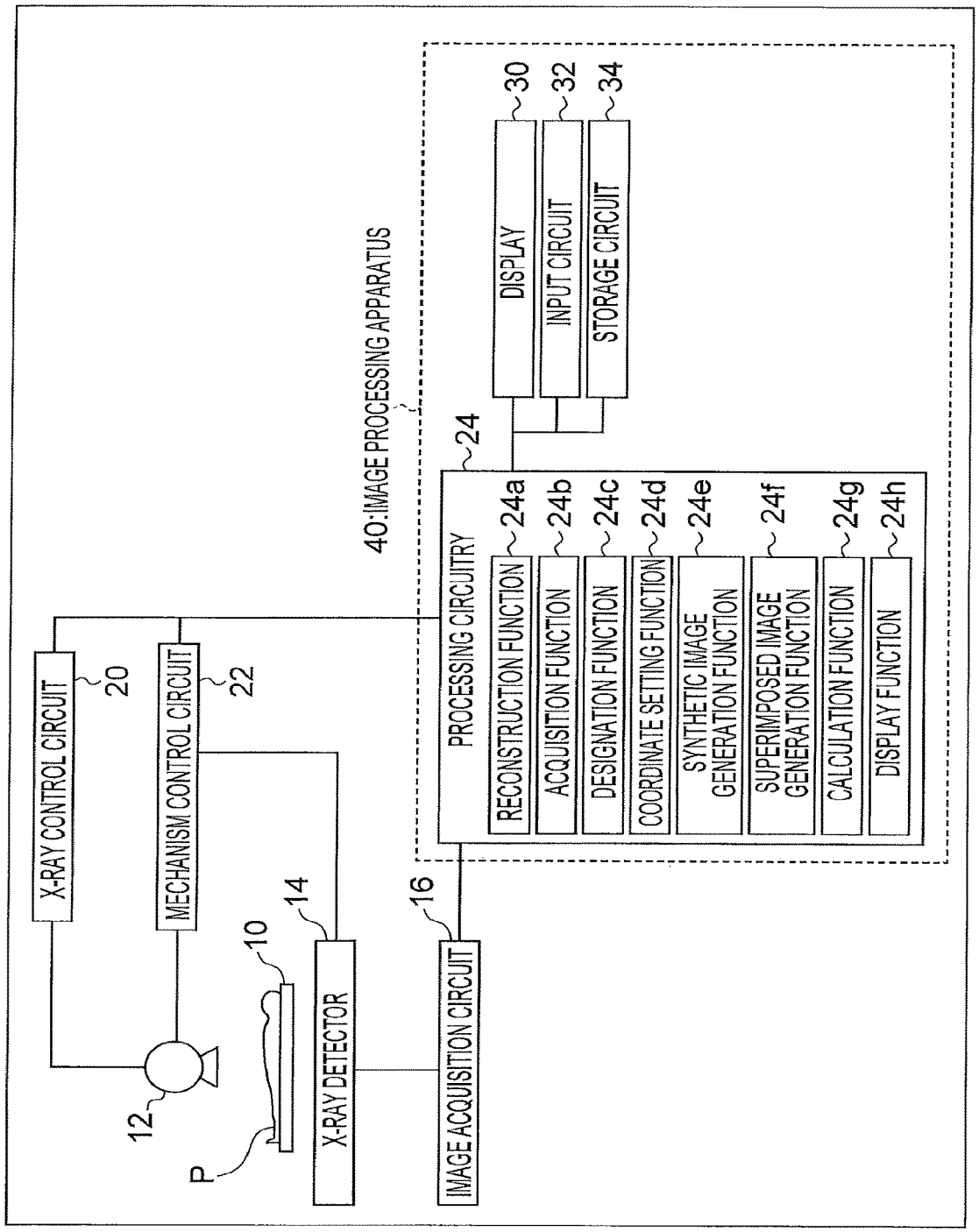
FIG. 1 is a block diagram for explaining the entire configuration of an X-ray diagnostic apparatus according to an embodiment.

Hereinafter, an image processing apparatus, an X-ray diagnostic apparatus, and an image processing method according to embodiments will be described referring to the drawings. Note that components having substantially the same functions and configurations will be denoted by the same numerals and duplicated explanation will be made in a necessary case in the following explanation.

First Embodiment

FIG. 1 is a diagram for explaining the entire configuration of an X-ray diagnostic apparatus 1 according to a first embodiment. The X-ray diagnostic apparatus 1 illustrated in FIG. 1 is an example of a medical apparatus including an image processing apparatus in this embodiment, and the image processing apparatus according to this embodiment is applicable to various X-ray diagnostic apparatuses such as a general imaging apparatus and so on.

More specifically, the X-ray diagnostic apparatus 1 includes a support table 10, an X-ray tube 12, an X-ray detector 14, an image acquisition circuit 16, an X-ray control circuit 20, a mechanism control circuit 22, processing circuitry 24, a display 30, an input circuit 32, and a storage circuit 34.

On the support table 10, a subject P in a lying state is supported. The X-ray diagnostic apparatus 1 according to this embodiment is configured such that the subject P lies down on his/her back on the support table 10 and the whole body of the subject P can be imaged with X-rays.

The X-ray tube 12, to which a high voltage and a filament current are supplied from a high-voltage generator under control of the X-ray control circuit 20, generates an X-ray on the basis of the high voltage and the filament current. The X-ray tube 12 can perform X-ray imaging on the whole body from the head to the feet of the subject P, in cooperation with X-ray detector 14 on the basis of control by the mechanism control circuit 22. Such imaging is called X-ray long range imaging.

The X-ray detector 14 is composed of, for example, a flat panel detector (FPD) having a plurality of pixels two-dimensionally arrayed, and each of the pixels detects an X-ray from the X-ray tube 12 transmitted through the subject P and converts the detected X-ray into an electrical signal. This electrical signal is outputted to the image acquisition circuit 16.

The image acquisition circuit 16 converts the electrical signal being an analog signal inputted from the X-ray detector 14 into digital data to generate projection data in a not-illustrated analog digital converter. In this embodiment, the projection data is a two-dimensional image obtained by imaging the subject P. Control by the mechanism control circuit 22 moves the X-ray tube 12 and the X-ray detector 14 facing each other, from the head to the feet of the subject P, thereby sequentially generating a plurality of pieces of projection data. The plurality of pieces of projection data generated are outputted to the processing circuitry 24 as needed.

The X-ray control circuit 20 controls the X-ray tube 12 on the basis of a control instruction from the processing circuitry 24 and generates the high voltage and the filament current according to an X-ray condition to cause the X-ray tube 12 to generate an X-ray. The mechanism control circuit 22 controls a moving mechanism for the X-ray tube 12 and the X-ray detector 14 on the basis of a control instruction from the processing circuitry 24 to irradiate the head to the feet of the subject P with X-rays, thereby generating the plurality of pieces of projection data.

The processing circuitry 24 is a control circuit that performs overall control of the X-ray diagnostic apparatus 1 and is also an arithmetic circuit that performs various arithmetic operations. For example, the processing circuitry 24 according to this embodiment includes a reconstruction function 24a, an acquisition function 24b, a designation function 24c, a coordinate setting function 24d, a synthetic image generation function 24e, a superimposed image generation function 24f, a calculation function 24g, and a display function 24h. The acquisition function 24b corresponds to an acquirer in this embodiment, the designation function 24c corresponds to a designator in this embodiment, the coordinate setting function 24d corresponds to a coordinate setter in this embodiment, the synthetic image generation function 24e corresponds to a synthetic image generator in this embodiment, the superimposed image generation function 24f corresponds to a superimposed image generator in this embodiment, the calculation function 24g corresponds to a calculator in this embodiment, and the display function 24h corresponds to a display in this embodiment.

In the embodiment in FIG. 1, the processing functions performed in the reconstruction function 24a, the acquisition function 24b, the designation function 24c, the coordinate setting function 24d, the synthetic image generation function 24e, the superimposed image generation function 24f, the calculation function 24g, and the display function 24h are stored in the storage circuit 34, in forms of programs executable by a computer. The processing circuitry 24 is a circuit that reads the programs from the storage circuit 34 and executes the programs to thereby realize the functions corresponding to the respective programs. In other words, the processing circuit in a state of having read the programs has the functions illustrated in the processing circuitry 24 in FIG. 1. Note that FIG. 1 is illustrated such that the reconstruction function 24a, the acquisition function 24b, the designation function 24c, the coordinate setting function 24d, the synthetic image generation function 24e, the superimposed image generation function 24f, the calculation function 24g, and the display function 24h are realized by the single processing circuitry 24. However, a plurality of independent processing circuits may be combined to constitute the processing circuitry 24 so that the plurality of processing circuits can execute the programs to thereby realize the functions. The processing circuitry 24 in the first embodiment is one example of processing circuitry in the claims.

The reconstruction function 24a acquires the plurality of pieces of projection data from the image acquisition circuit 16, performs image processing such as image reconstruction thereon to generate a tomosynthesis image, and stores the tomosynthesis image into the storage circuit 34. The tomosynthesis image is composed of images of a plurality of slices, and one tomographic image in a vertical direction in the subject P constitutes one splice in this embodiment. In short, the tomosynthesis image is constituted as a set of a plurality of tomographic images.

Figure 2:
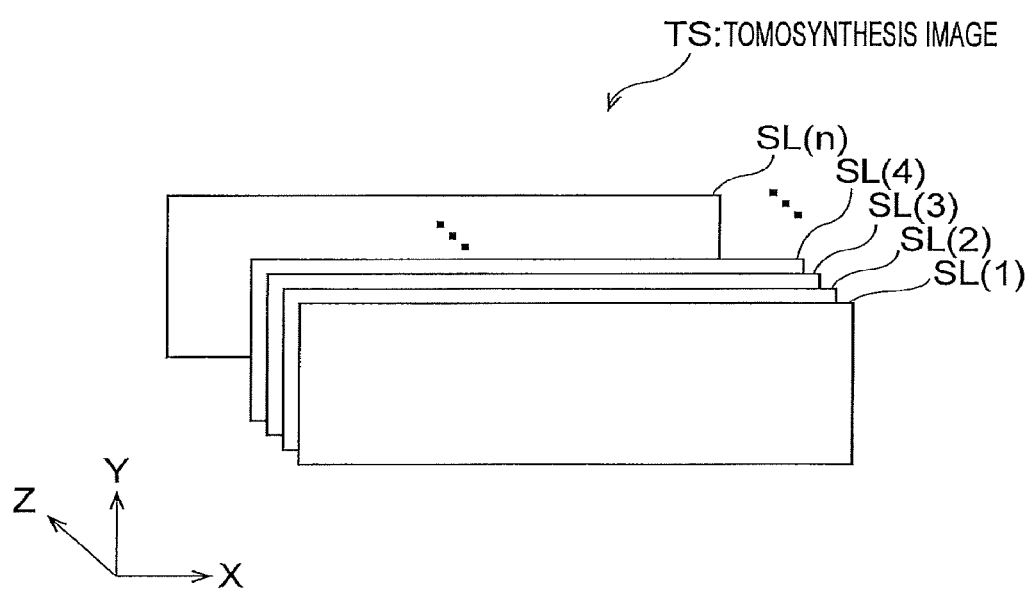
FIG. 2 is a diagram for explaining a data configuration of a tomosynthesis image generated by the X-ray diagnostic apparatus in FIG. 1.

FIG. 2 is a conceptual diagram for explaining the configuration of a tomosynthesis image TS according to this embodiment. As illustrated in FIG. 2, the tomosynthesis image TS is constituted including a plurality of almost parallel slices SL(1) to SL(n). In this embodiment, an image of one slice SL(X) is a tomographic image in the vertical direction of the subject P, and slices SL(1) to SL(n) constitute the three-dimensional image data of the whole body of the subject P. Here, the image of one slice is an image regarding a plane extending in an X-direction and a Y-direction in FIG. 2, and the slices SL(1) to SL(n) are arrayed in a Z-direction to realize a three-dimensional data structure. However, the data structure is not limited to this, but may be, for example, a data structure in which the image of one slice is an image in a plane extending in the X-direction and the Z-direction in FIG. 2 and the slices SL(1) to SL(n) are arrayed in the Y-direction. In any data structure, for example, tens to hundreds of slices constitute the three-dimensional image data in this embodiment.

Though details will be described later, the acquisition function 24b of the processing circuitry 24 illustrated in FIG. 1 has a function of acquiring, from the storage circuit 34, the data on the tomosynthesis image being three-dimensional medical image data constituted including a plurality of slices. The designation function 24c has a function of designating a first slice and a second slice from among the plurality of slices included in the tomosynthesis image, for example, on the basis of designation by a user. The coordinate setting function 24d has a function of setting first coordinates on an image of the first splice and setting second coordinates on an image of the second slice, for example, on the basis of the designation by the user or the like. The synthetic image generation function 24e has a function of generating a two-dimensional synthetic image on the basis of a tomosynthesis image being three-dimensional data in a region including the first slice and the second slice. The superimposed image generation function 24f has a function of generating a superimposed image in which an auxiliary figure generated by the calculation function 24g is superimposed on the synthetic image. The calculation function 24g has a function of calculating geometric parameters such as an angle and a length based on the auxiliary figure and creating the auxiliary figure such as a straight line or a curved line based on at least one of the first coordinates and the second coordinates. The display function 24h has a function of displaying the superimposed image and the geometric parameters together on the display 30.

The display 30 displays various kinds of images and information. For example, the display 30 displays a medical image (X-ray image) generated by the processing circuitry 24, a GUI (Graphical User Interface) or the like for accepting various operations from an operator and the like. In particular, in this embodiment, the display 30 displays the tomosynthesis image generated by the processing circuitry 24. In this embodiment, the display 30 is composed of, for example, a liquid crystal display, a CRT (Cathode Ray Tube) display or the like.

The input circuit 32 accepts various input operations from the operator, converts the accepted input operation into an electrical signal, and outputs the electrical signal to the processing circuitry 24. For example, the input circuit 32 accepts from the operator a collection condition when collecting the projection data, a reconstruction condition when reconstructing the projection data, an image processing condition when generating a post-processing image from the X-ray image and so on. For example, the input circuit 32 is realized by a mouse, a keyboard, a trackball, a manual switch, a foot switch, a button, a joystick or the like.

The storage circuit 34 is realized, for example, by a semiconductor memory element such as a RAM (Random Access Memory) or a flash memory, a hard disk, an optical disk or the like. The storage circuit 34 stores, for example, the projection data and reconstruction image data. In this embodiment, in particular, the tomosynthesis image made by performing image processing such as image reconstruction on the plurality of pieces projection data from the image acquisition circuit 16 is stored.

As described above, the processing circuitry 24 is composed of, for example, the processing circuit in this embodiment. The word processing circuit here means, for example, a CPU (Central Processing Unit), a GPU (Graphical Processing Unit), or a circuit such as an application specific integrated circuit (ASIC), a programmable logic device (for example, a simple programmable logic device: SPLD), a complex programmable logic device (CPLD), a field programmable gate array (FPGA) and the like. The processing circuit realizes the functions by reading and executing the programs stored in the storage circuit 34. Note that instead of storing the programs in the storage circuit 34, the programs may be directly installed in a circuit of the processing circuit. In this case, the processing circuit reads and executes the programs installed in the circuit to thereby realize the functions. Note that the processing circuitry 24 is not limited to the case of being configured as a single processing circuit, but a plurality of independent processing circuits may be combined together to constitute one processing circuit to realize the functions. Further, the plurality of components in FIG. 1 may be integrated into a single processing circuit to realize the functions.

Note that in the X-ray diagnostic apparatus 1 according to this embodiment, the processing circuitry 24, the display 30, the input circuit 32, and the storage circuit 34 constitute an image processing apparatus 40. The image processing apparatus 40 may be housed in one housing or may be housed separately in a plurality of housings. Besides, the image processing apparatus 40 may be constituted integrally with the X-ray diagnostic apparatus 1 or may be constituted separately from the X-ray diagnostic apparatus 1.

Next, diagnostic image generation processing executed in the X-ray diagnostic apparatus 1 according to this embodiment will be described based on FIG. 3. The diagnostic image generation processing illustrated in FIG. 3 is processing realized by the processing circuitry 24 reading and executing a diagnostic image generation processing program stored in the storage circuit 34.

Figure 3:
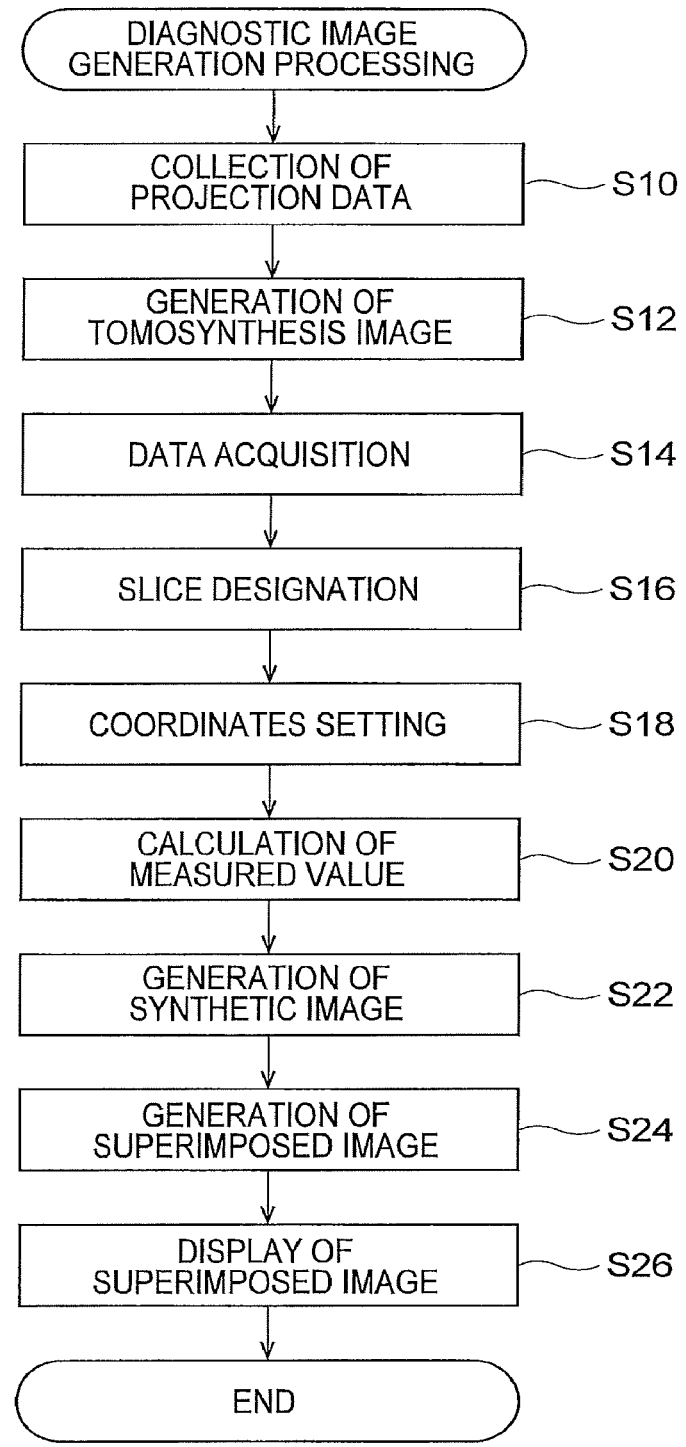
FIG. 3 is a diagram illustrating a flowchart for explaining diagnostic image generation processing executed in the X-ray diagnostic apparatus according to a first embodiment.

As illustrated in FIG. 3, the X-ray diagnostic apparatus 1 first collects the projection data for generating the tomosynthesis image (Step S10). The processing of collecting the projection data is processing executed by the image acquisition circuit 16 under control of the processing circuitry 24.

For example, the user operates the foot switch and the joystick of an operation unit provided in the input circuit 32 to input instructions for X-ray imaging and for collection of the projection data, into the X-ray control circuit 20 and the mechanism control circuit 22. In this embodiment, when the user operates the foot switch of the input circuit 32, a control signal is inputted via the processing circuitry 24 into the X-ray control circuit 20, and the X-ray control circuit 20 generates an X-ray from the X-ray tube 12 on the basis of the control signal. On the other hand, when the user operates the joystick of the input circuit 32, a control signal is inputted via the processing circuitry 24 into the mechanism control circuit 22, and the mechanism control circuit 22 moves the X-ray tube 12 or moves the X-ray detector 14 on the basis of the control signal. Further, the mechanism control circuit 22 detects positions and angles of the X-ray tube 12 and the X-ray detector 14, and inputs information on the positions and information on the angles into the processing circuitry 24.

The X-ray transmitted through the subject P under control of the X-ray control circuit 20 and the mechanism control circuit 22 is detected by the X-ray detector 14. The detected X-ray is converted into a digital signal and projection data is collected in the image acquisition circuit 16. The collected projection data is transmitted to the processing circuitry 24. The processing circuitry 24 stores the transmitted projection data together with positional information and angular information once into the storage circuit 34. The processing circuitry 24, however, does not have to store the transmitted projection data into the storage circuit 34 but may perform generation of the tomosynthesis image (Step S12) subsequent thereto.

Next, the X-ray diagnostic apparatus 1 performs generation of the tomosynthesis image (Step S12). The generation of the tomosynthesis image is realized by the reconstruction function 24a of the processing circuitry 24. More specifically, the processing circuitry 24 acquires the projection data from the storage circuit 34 and performs image reconstruction processing on the projection data to thereby generate data on the tomosynthesis image. For the image reconstruction processing, an image reconstruction algorithm such as existing Filtered Back Projection or Iterative Reconstruction is used. The generated data on the tomosynthesis image is stored in the storage circuit 34. However, the processing circuitry 24 does not have to store the generated data on the tomosynthesis image into the storage circuit 34 but may perform later-described processing of designating a slice (Step S16).

Next, the X-ray diagnostic apparatus 1 performs processing of acquiring the data on the tomosynthesis image (Step S14). The processing of acquiring the data on the tomosynthesis image is realized by the acquisition function 24b in the processing circuitry 24. More specifically, the processing circuitry 24 reads and acquires the data on the tomosynthesis image from the storage circuit 34. Note that the processing circuitry 24 does not acquire the data on the tomosynthesis image from the storage circuit 34 but can directly acquire the data on the tomosynthesis image from the above-described processing of generating the tomosynthesis image (Step S12).

Next, the X-ray diagnostic apparatus 1 performs processing of designating two slices from the data on the tomosynthesis image constituted including the plurality of slices (Step S16), and performs processing of setting coordinates on each of the slices (Step S18). The processing of designating the two slices is realized by the designation function 24c of the processing circuitry 24, and the function of setting the coordinates on each of the slices is realized by the coordinate setting function 24d of the processing circuitry 24.

More specifically, in this embodiment, the data on the tomosynthesis image is constituted of, for example, tens to hundreds of slices as illustrated in FIG. 2. The processing circuitry 24 causes the user to designate one slice from the slices as the first slice and set the first coordinates being one set of coordinates on the image of the first slice. The processing circuitry 24 further causes the user to designate another slice as the second slice and set the second coordinates being one set of coordinates on the second slice. In this embodiment, for example, in order to evaluate a pelvis distortion, the first coordinates on the first slice indicate a center position of the femoral head, and the second coordinates on the second slice indicate an upper-end center position of the sacrum. In other words, in the present embodiment, the femoral head is a first element, the first coordinates are coordinates of the first element, the sacrum is a second element, and the second coordinates are coordinates of the second element.

Figure 4:
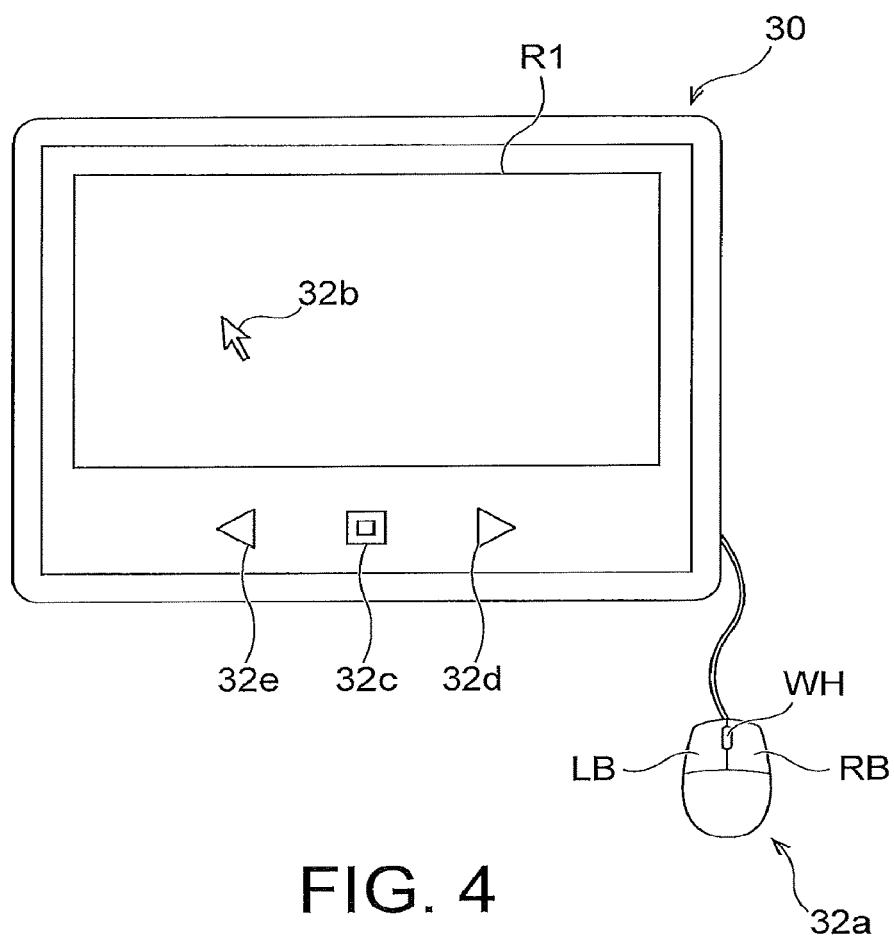
FIG. 4 is a view illustrating a display in FIG. 1 and a mouse being an example of an input circuit.

There are various conceivable ways to designate the slice and methods of setting the coordinates. FIG. 4 is a view for explaining one example of the methods of designating the slice and setting the coordinates in the X-ray diagnostic apparatus 1 according to this embodiment.

As illustrated in FIG. 4, for example, the images of the plurality of slices are displayed sequentially from the slice SL(1) to the slice SL(n) in an image display region R1 on the display 30 and reproduced as a moving image. The user operates a mouse 32a being one example of the input circuit 32 to move a pointer 32b on the display 30, and operates a stop button 32c, a moving image reproduction button 32d, and a moving image reverse button 32e for reproduction of the moving image. For example, in a state of reproducing the moving image in the image display region R1, the user moves the pointer 32b onto the stop button 32c at timing when the slice determined that the femoral head can be observed most clearly is displayed, and clicks a left button LB of the mouse 32a. This stops the reproduction of the moving image at that timing, and designates the image of the slice displayed at the stop as the first slice where the femoral head is displayed.

Subsequently, the user clicks the center of the femoral head on the image of the slice where the femoral head is displayed. In other words, the user operates the mouse 32a to move the pointer 32b in the image display region R1 in which the image of the slice is displayed as a still image to thereby position the pointer 32b at the center of the femoral head. Clicking the left button LB of the mouse 32a in this state sets the center of the femoral head as the first coordinates.

Figure 5:
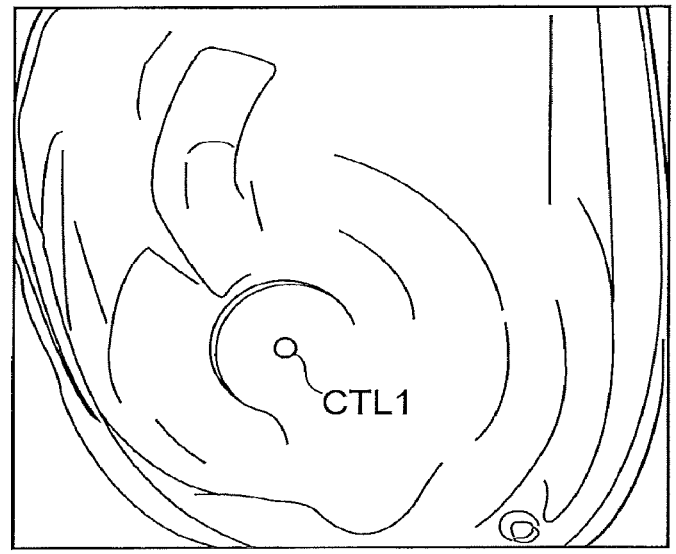
FIG. 5 is a view illustrating an image of a state where a center of the femoral head is set on an image of a first slice.

FIG. 5 illustrates a state where an image of the femoral head is designated as the first slice and a center CTL1 of the femoral head is set on the image of the femoral head. As is found from FIG. 5, the user moves the pointer 32b from the image of the first slice where the femoral head is displayed to the position of the center CTL1 of the femoral head, and clicks the left button LB of the mouse 32a to thereby set the coordinates of the center CTL1 as the first coordinates.

Subsequently, the user clicks the moving image reproduction button 32d to restart the reproduction of the moving image, designates a slice determined that the sacrum can be observed most clearly as the second slice by the same method, and clicks the upper-end center of the sacrum on the image of the second slice to thereby set the second coordinates.

Figure 6:
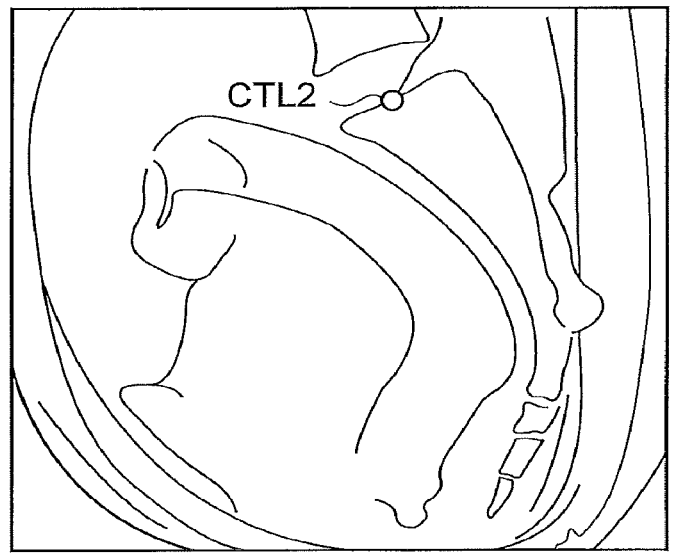
FIG. 6 is a view illustrating an image of a state where an upper-end center of the sacrum is set on an image of a second slice.

FIG. 6 illustrates a state where an image of the sacrum is designated as the second slice and an upper-end center CTL2 of the sacrum is set on the image of the sacrum. As is found from FIG. 6, the user moves the pointer 32b from the image of the second slice where the sacrum is displayed to the position of the center CTL2 at the upper end of the sacrum, and clicks the left button LB of the mouse 32a to thereby set the coordinates of the center CTL2 as the second coordinates. Note that the left button LB is used as a decision button in the operation of the mouse 32a in this embodiment, but a right button RB may be used as the decision button in place of the left button LB.

Through the above operations, the user can designate the first slice and set the first coordinates on the designated first slice, and designate the second slice and set the second coordinates on the designated second slice. In this embodiment, information is held with information indicating what number slice it is set as a Z-coordinate and with information indicating which position it is on the slice image set as an X-coordinate and a Y-coordinate. In short, the user will designate two sets of X-coordinate, Y-coordinate, and Z-coordinate by Step S16 and Step S18 in this embodiment.

Note that the method of designating the first slice and the second slice and the method of setting the first coordinates and the second coordinates are not limited to the above examples. For example, at the time when displaying the images of the plurality of slices SL(1) to SL(n) in the image display region R1 on the display 30 in FIG. 4, the user may rotate a wheel button WH of the mouse 32a so that the images of the slices are sequentially shifted following the rotation of the wheel button WH. For example, it is only necessary to sequentially increase the number of the slice to be displayed in the image display region R1 when rotating the wheel button WH forward, whereas to sequentially decrease the number of the slice to be displayed in the image display region R1 when rotating the wheel button WH backward. As a matter of course, the rotation direction of the wheel button WH may be reversed. More specifically, it is also adoptable to sequentially increase the number of the slice to be displayed in the image display region R1 when rotating the wheel button WH backward, whereas to sequentially decrease the number of the slice to be displayed in the image display region R1 when rotating the wheel button WH forward.

In this case, the user stops the rotation of the wheel button WH at the slice determined that the femoral head can be observed most clearly and clicks the center CTL1 of the femoral head, and is thereby supposed to perform both the designation of the first slice and the setting of the first coordinates. Similarly, the user stops the rotation of the wheel button WH at the slice determined that the sacrum can be observed most clearly and clicks the upper-end center CTL2 of the sacrum, and is thereby supposed to perform both the designation of the second slice and the setting of the second coordinates.

Further, the user does not manually designate a slice and set coordinates, but the X-ray diagnostic apparatus 1 may be configured to automatically designate a slice and set coordinates by image analysis. More specifically, the X-ray diagnostic apparatus 1 may be configured to perform image analysis of the tomosynthesis image including the plurality of slices, and to systematically designate an image in which the femoral head can be observed most clearly as the first slice and set its center CTL1 as the first coordinates and to systematically designate an image in which the sacrum can be observed most clearly as the second slice and set its upper-end center CTL2 as the second coordinates. More specifically, the X-ray diagnostic apparatus 1 performs overall data analysis on the tomosynthesis image to systematically designate an image suitable for observation of the femoral head as the first slice and systematically designate an image suitable for observation of the sacrum as the second slice, and then performs image analysis on the first slice and the second slice to systematically set the center of the femoral head in the first slice as the first coordinates and to systematically set the upper-end center of the sacrum in the second slice as the second coordinates.

Note that the unit of the first coordinates set in the image of the first slice and the unit of the second coordinates set in the image of the second slice may coincide with or different from that of the pixel of the image. In the case where the unit of the pixel and the unit of the coordinates coincide with each other, one set of coordinates will be allocated to one pixel. A predictable example where the units of the pixel and the coordinates are different is a case that coordinates are set for each of four regions defined by 2×2 pixels in the image of the slice. The correspondence between the coordinates and the pixel is arbitrarily set depending on the pixel density on the image, the size of a coordinate space to be set or the like.

Figure 7:
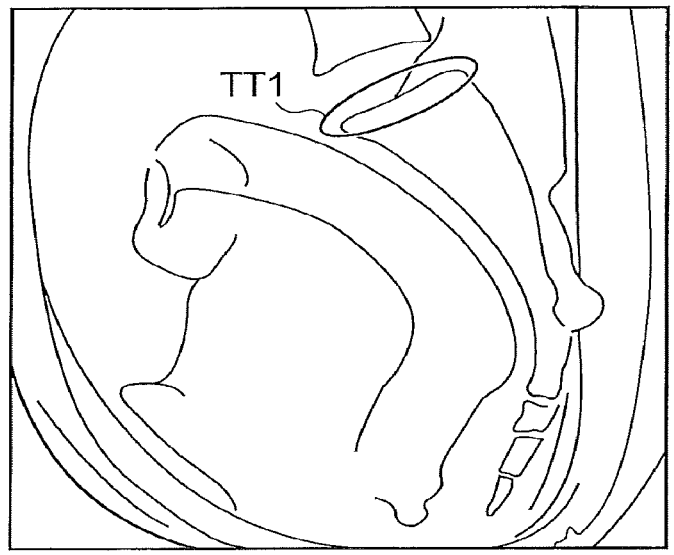
FIG. 7 is a view illustrating an image for explaining a position of the sacrum centrum in the image of the second slice.

Next, as illustrated in FIG. 3, the X-ray diagnostic apparatus 1 calculates a measured value on the basis of the images of the two slices (Step S20). The processing of calculating the measured value is realized by the calculation function 24g of the processing circuitry 24. In this embodiment, the processing circuitry 24 first detects a line of the sacrum centrum using the image of the second slice. FIG. 7 is a view for explaining the processing of detecting the line of a sacrum centrum TT1 in the image of the second slice. To detect the line of the sacrum centrum TT1, the processing circuitry 24 cuts out an image around the second coordinates in the image of the second slice, and performs differential processing, threshold processing, Hough transformation processing, peak detection processing, and Hough reverse transformation processing with only peak, on the cutout image to detect the line of the sacrum centrum TT1.

Figure 8:
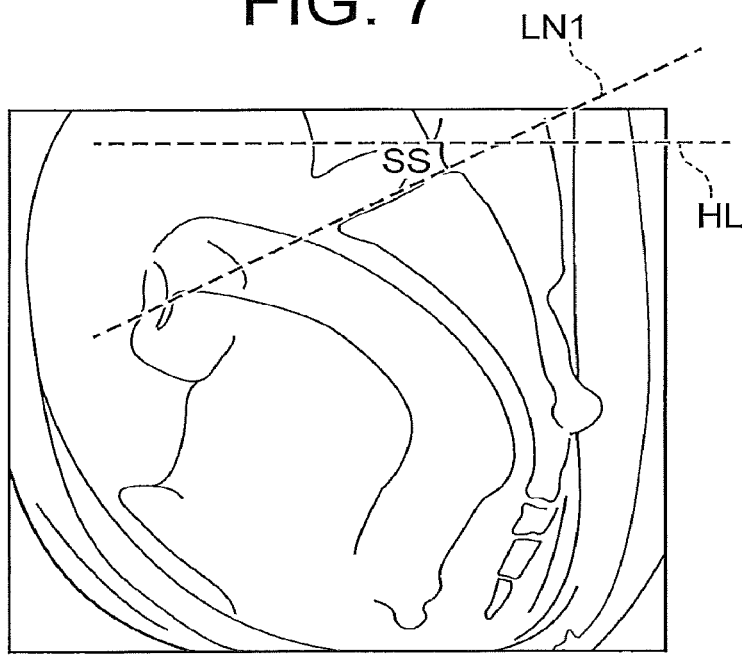
FIG. 8 is a view illustrating an image for explaining an angle formed between a line of the sacrum centrum and a horizontal line HL in the image of the second slice.

FIG. 8 is a view illustrating an example of a state where a line LN1 of the sacrum centrum TT1 is detected and the line LN1 is drawn in the image of the second slice. As illustrated in FIG. 8, the line LN1 of the sacrum centrum TT1 is a line defined by an angle of the sacrum centrum TT1. Further, in this embodiment, the calculation function 24g of the processing circuitry 24 calculates an angle SS formed between the line LN1 of the sacrum centrum TT1 and a horizontal line HL.

Figure 9:
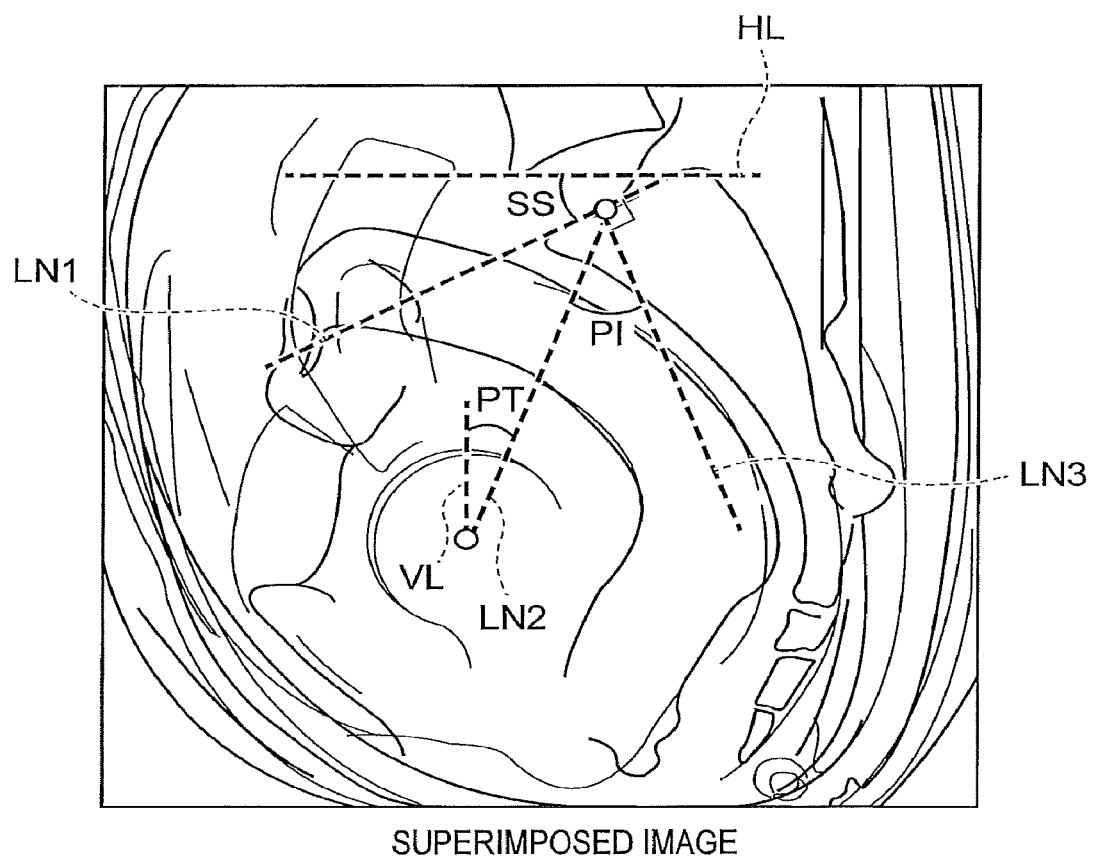
FIG. 9 is a view illustrating an image for explaining a superimposed image in which an auxiliary figure is superimposed on a synthetic image.

Next, the calculation function 24g of the processing circuitry 24 calculates an angle PT. FIG. 9 is a view for explaining the calculation of the angle PT. More specifically, the processing circuitry 24 calculates an auxiliary line LN2 linking an X-coordinate and a Y-coordinate of the center CTL1 of the femoral head in the image of the first slice and an X-coordinate and a Y-coordinate of the upper-end center CTL2 of the sacrum in the image of the second slice. Then, the processing circuitry 24 calculates the angle PT formed between the auxiliary line LN2 and a vertical line VL. Note that the auxiliary line LN2 corresponds to a first auxiliary line in this embodiment.

Next, the calculation function 24g of the processing circuitry 24 calculates an angle PI illustrated in FIG. 9. More specifically, the processing circuitry 24 calculates an auxiliary line LN3 vertical to the line LN1 of the sacrum centrum TT1. Then, the processing circuitry 24 calculates the angle PI formed between the auxiliary line LN3 and the auxiliary line LN2. In other words, the angle PI is the angle between the auxiliary line LN3 vertical to the line LN1 of the sacrum centrum TT1 and the auxiliary line LN2 linking the upper-end center CTL2 of the sacrum and the center CTL1 of the femoral head, and the processing circuitry 24 calculates this angle PI. Note that the auxiliary line LN3 corresponds to a second auxiliary line in this embodiment.

Next, as illustrated in FIG. 3, the X-ray diagnostic apparatus 1 performs processing of generating a synthetic image (Step S22). The processing of generating the synthetic image is realized by the synthetic image generation function 24e of the processing circuitry 24.

In this embodiment, the processing circuitry 24 synthesizes, for example, the image of the first slice and the image of the second slice to generate the synthetic image. More specifically, the processing circuitry 24 calculates an average of a pixel value in the image of the first slice and a pixel value in the image of the second slice to generate the synthetic image. The processing circuitry 24 may store the generated synthetic image once in the storage circuit 34, or does not have to store the generated synthetic image in the storage circuit 34 but may perform the processing of generating the superimposed image (Step S24) subsequent thereto.

Alternatively, the generation of the synthetic image may be performed by synthesizing an image of a slice near the first slice including the first slice and an image of a slice near the second slice including the second slice. In this case, in a case of synthesizing five slices SL(X−2) to SL(X+2) in total composed of a slice SL(x) as the first slice and two slices each prior and subsequent thereto in the data structure of the tomosynthesis image in FIG. 2, the slices may be synthesized after the same weighting coefficient is set to the slices and then weighting averaging is performed, or the slices may be synthesized after different weighting coefficients are set to the slices and then weighting average is performed. In the case of synthesizing the images with the different weighting coefficients, it is also possible, for example, to set a weighting coefficient of 0.1 to each of the slice SL(X−2) and the slice SL(X+2), set a weighting coefficient of 0.2 to each of the slice SL(X−1) and the slice SL(X+1), and set a weighting coefficient of 0.4 to the slice SL(X). As a matter of course, an arbitrary number of slices may be used in generating the synthetic image after setting the weighting coefficients.

Furthermore, it is also possible to set weighting coefficients to all of the slices SL(1) to SL(n) and synthesize images of all of the slices SL(1) to SL(n). For example, it is also possible to set weighting coefficients such that a weighting coefficient of 0.3 is set to each of the first slice SL(X1) and the second slice SL(X2) among the slices SL(1) to SL(n) and a remaining weighting coefficient of 0.4 is evenly allocated to the remaining slices. In other words, in this embodiment, the synthetic image generation function 24e of the processing circuitry 24 can generate a synthetic image by synthesizing the two-dimensional images on the basis of the data on the tomosynthesis image in a region including the first slice and the second slice in the data on the tomosynthesis image constituted of the slices SL(1) to SL(n). Note that the weighting coefficient set at Step S22 corresponds to a first weighting coefficient in this embodiment.

Next, as illustrated in FIG. 3, the X-ray diagnostic apparatus 1 superimposes the auxiliary figure such as the auxiliary lines used in the calculation of the measured value at Step S20, on the synthetic image generated at Step S22 to generate a superimposed image (Step S24). The processing of superimposing the auxiliary figure on the synthetic image to generate the superimposed image is realized by the superimposed image generation function 24f of the processing circuitry 24.

Explaining the above image in FIG. 9 used as an example, the superimposed image is generated by superimposing the line LN1 of the sacrum centrum, the auxiliary lines LN2, LN3, the horizontal line HL, and the vertical line VL on the synthetic image. Though an arbitrary auxiliary figure may be superimposed on the synthetic image, an image to help the user make a diagnosis based on the synthetic image is superimposed on the synthetic image. In other words, the processing circuitry 24 generates an auxiliary figure useful for the diagnosis on the basis of at least one of the first coordinates and the second coordinates, and superimposes the generated auxiliary figure on the synthetic image.

The synthetic image generated at Step S24 may be once stored for holding recording in the storage circuit 34, or does not have to be stored in the storage circuit 34 but may be displayed as it is in processing of displaying the superimposed image (Step S26) subsequent thereto. At the time when storing the superimposed image into the storage circuit 34, the values of the X-coordinates, Y-coordinates, and Z-coordinates of the first coordinates and the second coordinates can be stored as accompanying information together with the superimposed image, and the measured values such as the angle SS, the angle PT, and the angle PI calculated at Step S20 can be stored as accompanying information together with the superimposed image. Though arbitrary information may be stored as accompanying information, information useful at the time when the user makes a diagnosis afterwards using the stored superimposed image only needs to be stored in an accompanying manner.

Next, the X-ray diagnostic apparatus 1 displays the superimposed image generated at Step S24 (Step S26). The processing of displaying the superimposed image is realized by the display function 24h of the processing circuitry 24.

Figure 10:
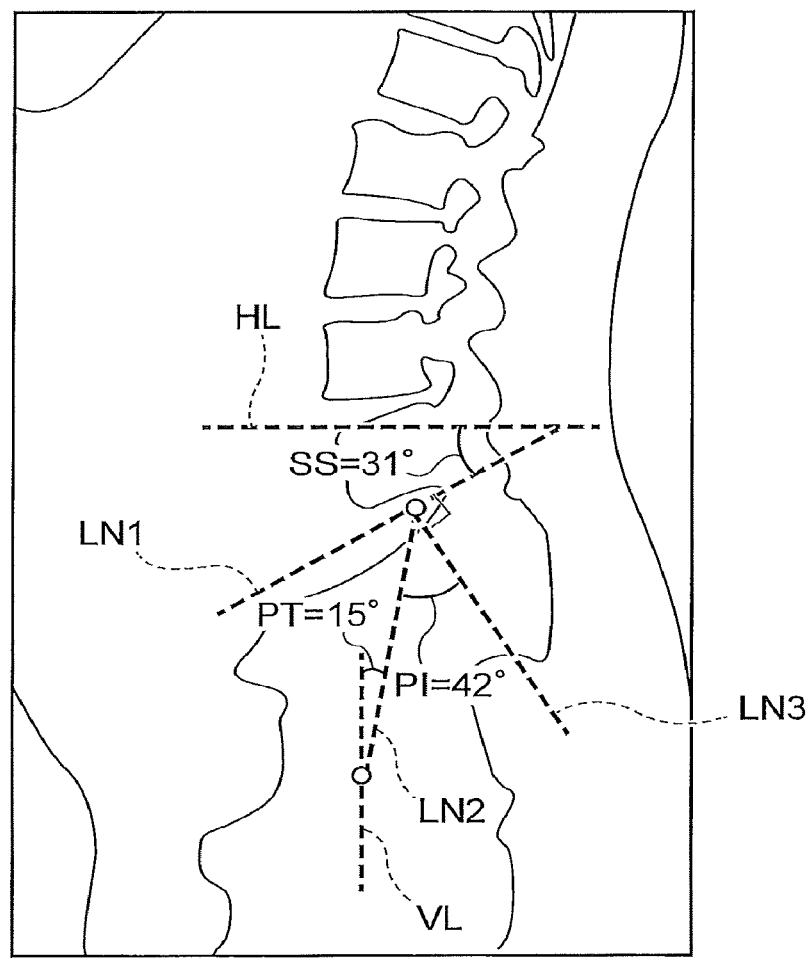
FIG. 10 is a view illustrating an example of the superimposed image displayed on the display in FIG. 1.

FIG. 10 is a view illustrating an example of the superimposed image displayed on the display 30 of the X-ray diagnostic apparatus 1 according to this embodiment. As illustrated in FIG. 10, in this embodiment, the line LN1 of the sacrum centrum, the auxiliary lines LN2, LN3, the horizontal line HL, and the vertical line VL which are examples of the auxiliary figure are displayed superimposed on the synthetic image generated based on the data on the tomosynthesis image. Besides, as the geometric parameters, an angle SS=31°, an angle PT=15°, and an angle PI=42° are displayed.

Note that those angles are examples of the geometric parameter when an evaluation target is the pelvis distortion, and geometric parameters useful when the user makes a diagnosis based on the synthetic image can be displayed together with the superimposed image. Therefore, the aspect of display of the geometric parameters can be realized not by displaying the geometric parameters superimposed on the superimposed image but by displaying the geometric parameters as a numerical value list, for example, in a region outside the superimposed image. Further, the display of the geometric parameters is not always necessary, and it is also possible not to display the geometric parameters.

Further, the information displayed as the geometric parameters by the processing circuitry 24 is not limited to the measured value calculated at Step S20, but other useful information to evaluate the evaluation target may be displayed as the geometric parameter. For example, in the case where the user inputs a numerical value calculated uniquely based on the displayed superimposed image into the X-ray diagnostic apparatus 1, the inputted numerical value may be displayed as a geometric parameter together with the superimposed image.

With the processing of displaying the superimposed image (Step S26), the diagnostic image generation processing according to this embodiment ends. Therefore, when determining that the diagnostic image necessary for a diagnosis of the pelvis distortion has not been acquired, the user can operate again the operation unit provided in the input circuit 32 to instruct X-ray imaging and collection of imaging data. On the other hand, when determining that the diagnostic image necessary for a diagnosis has been acquired, the user can begin preparation for imaging of a next subject P.

As described above, the X-ray diagnostic apparatus 1 according to this embodiment is configured to designate the first slice and the second slice on the basis of the data on the tomosynthesis image being the three-dimensional medical image data including the plurality of slices, generate the synthetic image on the basis of the data on the tomosynthesis image in the region including the first slice and the second slice, and generate the superimposed image in which the auxiliary figure necessary for a diagnosis is superimposed on the synthetic image. Therefore, the three-dimensional image data included in the different slices such as the femoral head and the sacrum can be generated as the two-dimensional image data in a state of facilitating the diagnosis. This makes it possible to easily hold the image as an imaging record.

Further, since the superimposed image in which the auxiliary figure is superimposed on the synthetic image can be obtained, the user can more easily make a diagnosis on the basis of the auxiliary figure. In other words, the user can easily visually grasp the angle SS, the angle PT, and the angle PI on the basis of the line LN1 of the sacrum centrum, the auxiliary lines LN2, LN3, the horizontal line HL, and the vertical line VL displayed in the superimposed image. Therefore, it is possible to evaluate the pelvis distortion of the evaluation target based on the superimposed image or based on the auxiliary figure or the geometric parameter displayed on the superimposed image.

Note that though the first coordinates and the second coordinates are set by the position of the pointer 32b of the mouse 32a in the above processing of setting the coordinates at Step S18, the first coordinates and the second coordinates may be set by using an auxiliary figure such as a line segment or the like. For example, the coordinate setting function 24d of the processing circuitry 24 may cause the user to draw the line LN1 of the sacrum centrum and the auxiliary line LN3 being the vertical line to the line LN1 on the screen in the image in FIG. 9 to thereby set the X-coordinate and the Y-coordinate at the second coordinates. In this case, the intersection of the line LN1 and the auxiliary line LN3 is set as the X-coordinate and the Y-coordinate of the second coordinates.

Second Embodiment

In the above first embodiment, the pointing for setting the center CTL1 of the femoral head is performed only once. However, since there are femoral heads on both right and left sides, a second embodiment is configured such that even when center coordinates of the right and left femoral heads cannot be aligned with each other, appropriate synthetic image and superimposed image are generated by pointing each of the center of the femoral head on the right side and the center of the femoral head on the left side. Hereinafter, portions different from those in the first embodiment will be described.

Figure 11:
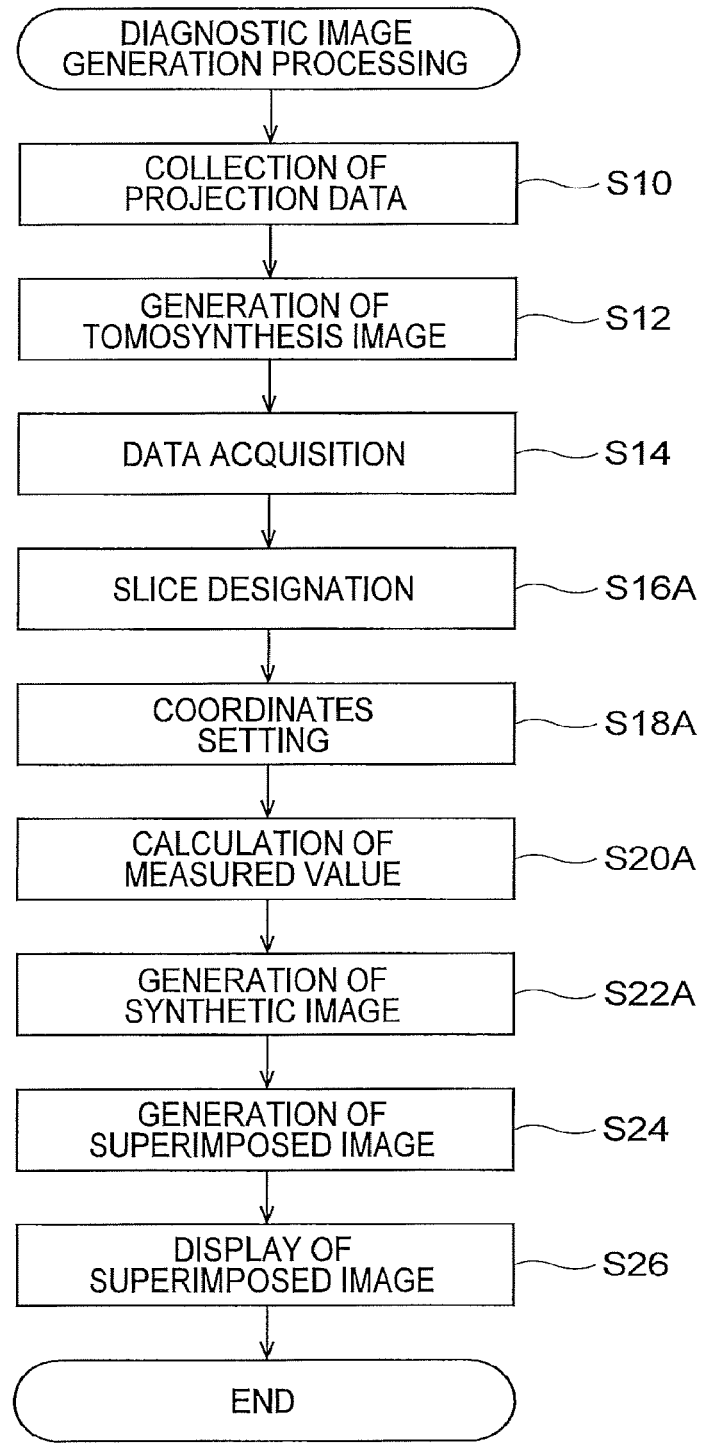
FIG. 11 is a diagram illustrating a flowchart for explaining diagnostic image generation processing executed in an X-ray diagnostic apparatus according to a second embodiment.

FIG. 11 is a diagram illustrating a flowchart for explaining diagnostic image generation processing according to the second embodiment, and is a diagram corresponding to FIG. 3 in the above first embodiment. As illustrated in FIG. 11, Step S16A to Step S22A in the diagnostic image generation processing according to this embodiment are different from Step S16 to Step S22 in the above first embodiment.

As illustrated in FIG. 11, in processing of designating a slice at Step S16A and processing of setting coordinates at Step S18A in this embodiment, the designation function 24c and the coordinate setting function 24d of the processing circuitry 24 cause the user to designate the first slice and set the center of the femoral head on the right side as the first coordinates, to designate the second slice and set the upper-end center of the sacrum as the second coordinates, and to designate a third slice and set the center of the femoral head on the left side (Step S16A, Step S18A).

Figure 12:
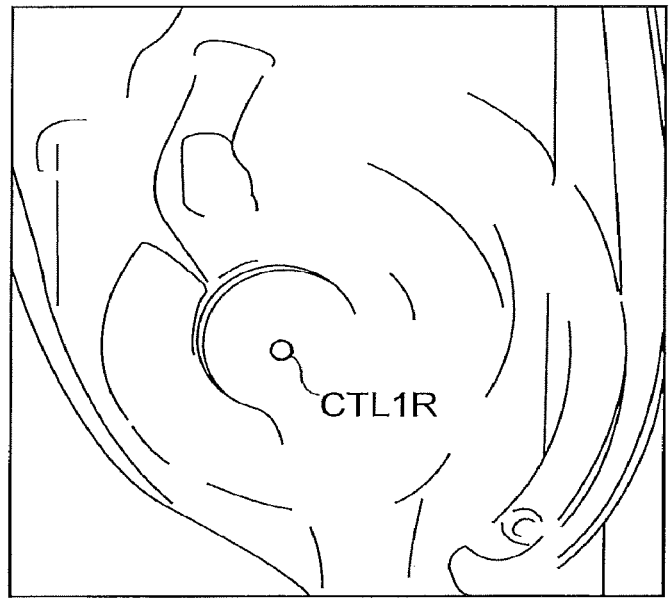
FIG. 12 is a view illustrating an image in a state where a center of the femoral head on the right side is set in the image of the first slice.
Figure 13:
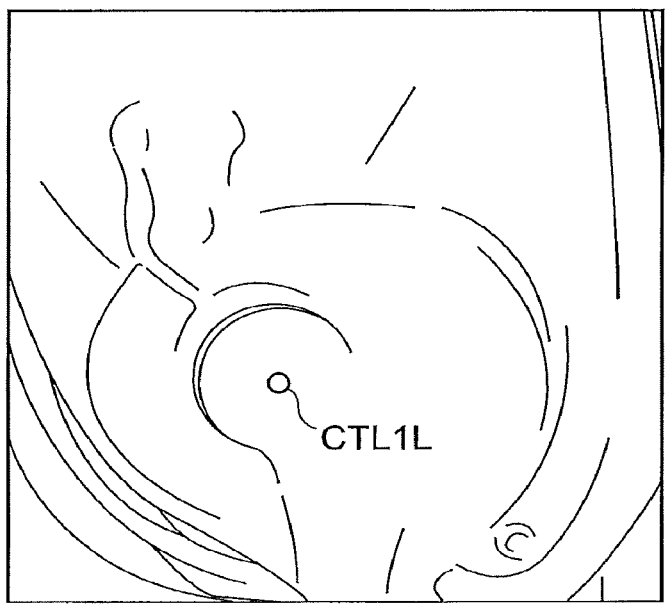
FIG. 13 is a view illustrating an image in a state where a center of the femoral head on the left side is set in an image of a third slice.

FIG. 12 is a view illustrating an example of an image in a state where the user sets a center CTL1R of the femoral head on the right side in the first slice, and FIG. 13 is a view illustrating an example of an image in a state where the user sets a center CTL1L of the femoral head on the left side in the third slice. The center CTL1R of the femoral head on the right side is located at the first coordinates, and the center CTL1L of the femoral head on the left side is located at third coordinates. Note that as described above, there are various aspects in the method of designating the first slice and the third slice and in the method of setting the center CTL1R of the femoral head on the right side and the center CTL1L of the femoral head on the left side, as described in the first embodiment. Besides, the method of setting the second coordinates in the second slice is the same as that in the first embodiment, and therefore description thereof will be omitted here. Besides, as described in the first embodiment, the center CTL1R of the femoral head on the right side and the center CTL1L of the femoral head on the left side are not set by the user but systematically settable by image analysis by the designation function 24c and the coordinate setting function 24d is as described above.

Next, as illustrated in FIG. 11, at Step S20A, the calculation function 24g of the processing circuitry 24 calculates an average value of the coordinates of the center CTL1R of the femoral head on the right side and the coordinates of the center CTL1L of the femoral head on the left side, and regards the average value as the center CTL1 of the femoral heads. In other words, the calculation function 24g calculates the average of the first coordinates and the third coordinates and calculates a measured value as in the above first embodiment using the average as the center CTL1 of the femoral head. The measured value can be calculated using concrete mathematical expressions such as X-coordinate= $(X1+X3)/2$, Y-coordinate= $(Y1+Y3)/2$ of the center CTL1 of the femoral head. Then, the processing circuitry 24 uses the calculated center CTL1 of the femoral head to generate the line LN1 of the sacrum centrum, the auxiliary lines LN2, LN3, the horizontal line HL, and the vertical line VL being the auxiliary figure, and calculates the angle SS, the angle PT, and the angle PI as in the first embodiment.

Note that the average value of the first coordinates and the third coordinates is calculated and the measured value is calculated based on coordinates of the calculated average value in the second embodiment, but, if necessary, the measured value may be calculated also using the third coordinates to generate the auxiliary figure. Alternatively, it is adoptable that an average value of the second coordinates and the third coordinates is calculated and a measured value is calculated based on coordinates of the calculated average value to generate the auxiliary figure. More specifically, it is adoptable that at least two average values of the first coordinates, the second coordinates, and the third coordinates are calculated, the measured value being the geometric parameter is calculated using coordinates of the calculated average values to generate the auxiliary figure.

Next, as illustrated in FIG. 11, a synthetic image is generated at Step S22A on the basis of data on a tomosynthesis image in a region including three slices such as the first slice, the second slice, and the third slice. For example, the synthetic image is generated by setting a weighting coefficient to an image of the first slice to ⅓, setting a weighting coefficient to an image of the second slice to ⅓, and setting a weighting coefficient to an image of the third slice to ⅓. As a matter of course, the weighting coefficients to the slices may be different as described in the first embodiment. Further, there are various aspects in the method of generating the synthetic image as in the first embodiment. Note that the weighting coefficient set at Step S22A corresponds to the first weighting coefficient in this embodiment.

Processing other than that at Step S16A to Step S22A is the same as that in the above first embodiment, and its hardware configuration is also the same as that in above FIG. 1.

As described above, the X-ray diagnostic apparatus 1 according to this embodiment is configured to individually perform the setting of the first coordinates being the coordinates of the center CTL1R of the femoral head on the right side and the setting of the third coordinates being the coordinates of the center CTL1L of the femoral head on the left side, and thus can generate an appropriate synthetic image necessary for a diagnosis even when the femoral head on the right side and the femoral head on the left side are displaced from each other at the time of imaging for generating the data on the tomosynthesis image.

Further, the X-ray diagnostic apparatus 1 is configured to calculate the measured value being the geometric parameter using the average value of the coordinates of the center CTL1R of the femoral head on the right side and the coordinates of the center CTL1L of the femoral head on the left side to generate the auxiliary figure, and thus can calculate with a sufficient degree of accuracy the measured value being the geometric parameter necessary for a diagnosis even when the femoral head on the right side and the femoral head on the left side are displaced from each other and can appropriately superimpose the auxiliary figure on the synthetic image to generate the superimposed image.

Third Embodiment

Though the weighting coefficient is set for each slice in the above first embodiment and second embodiment, a third embodiment is configured to generate a synthetic image for further facilitating a diagnosis by changing a weighting coefficient of an image near pointed coordinates with a weighting coefficient of an image in another region eve in one slice. The third embodiment will be described as a modification example of the first embodiment below, but it is obvious to apply the same modification example also to the second embodiment.

Figure 14:
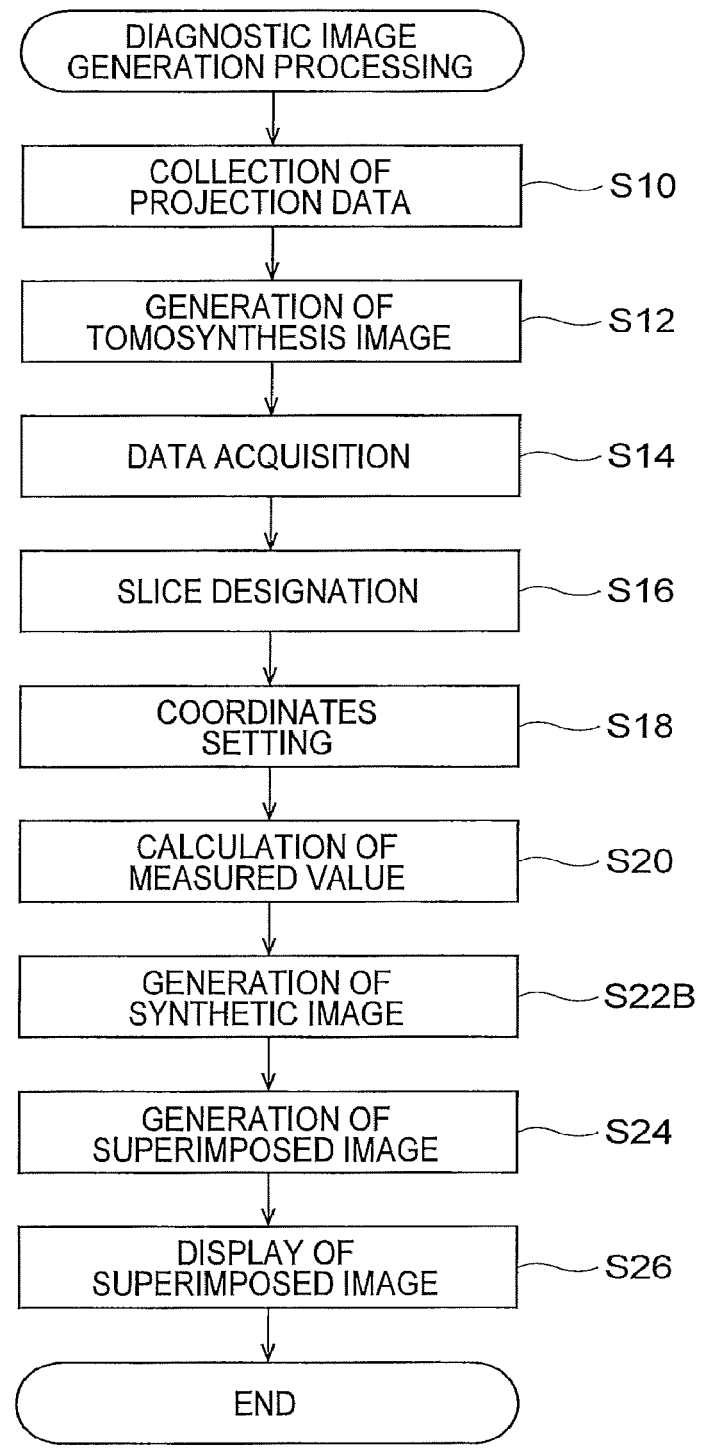
FIG. 14 is a diagram illustrating a flowchart for explaining diagnostic image generation processing executed in an X-ray diagnostic apparatus according to a third embodiment.

FIG. 14 is a diagram illustrating a flowchart for explaining diagnostic image generation processing according to the third embodiment, and is a diagram corresponding to FIG. 3 in the above first embodiment. As illustrated in FIG. 14, Step S22B in the diagnostic image generation processing according to this embodiment is different from Step S22 in the above first embodiment.

As illustrated in FIG. 14, in processing of generating a synthetic image at Step S22B, the synthetic image generation function 24e of the processing circuitry 24 sets a second weighting coefficient in a region near the first coordinates in the image of the first slice larger than a first weighting coefficient in another region in the image of the first slice and performs weighting averaging, thereby emphasizing an image near the femoral head. The synthetic image generation function 24e further sets a second weighting coefficient in a region near the second coordinates in the image of the second slice larger than a first weighting coefficient being a weighting coefficient in another region in the image of the second slice and performs weighting averaging, thereby emphasizing an image near the sacrum centrum. In other words, in this embodiment, the setting of the weighting coefficient is performed not only on the slice unit but also based on the position on a specific slice.

Figure 15:
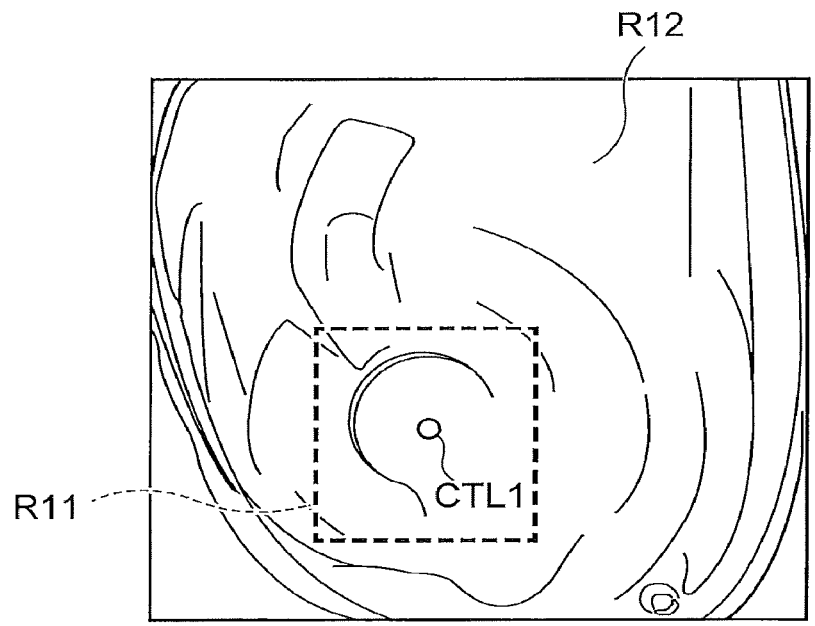
FIG. 15 is a view illustrating an image for explaining processing of setting a second weighting coefficient to a predetermined region including the center of the femoral head and setting a first weighting coefficient to the other region in the image of the first slice.
Figure 16:
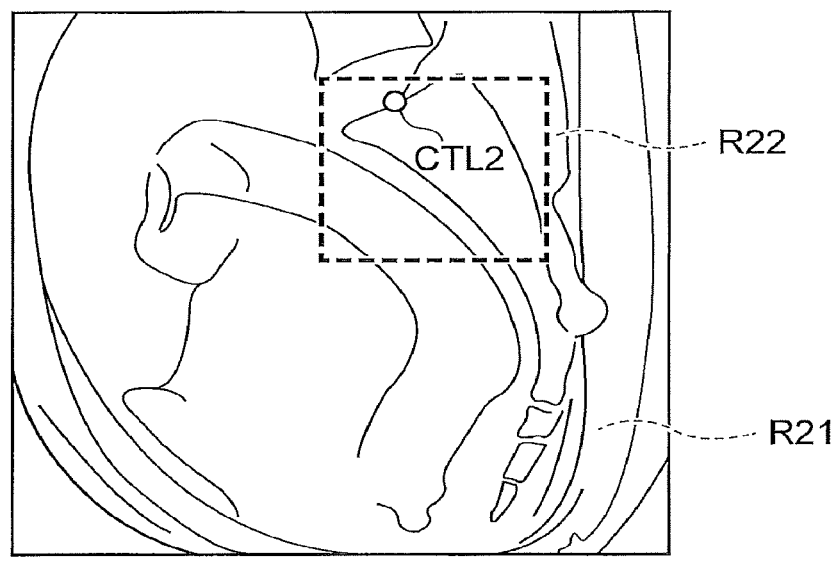
FIG. 16 is a view illustrating an image for explaining processing of setting a second weighting coefficient to a predetermined region including the upper-end center of the sacrum and setting a first weighting coefficient to the other region in the image of the second slice.

FIG. 15 is a view illustrating an example of an image for explaining the first weighting coefficient and the second weighting coefficient set in the image of the first slice, and FIG. 16 is a view illustrating an example of an image for explaining the first weighting coefficient and the second weighting coefficient set in the image of the second slice. As illustrated in FIG. 15, in the first slice, the second weighting coefficient is set to a predetermined region R11 including the first coordinates of the center CTL1 of the femoral head, and the first weighting coefficient is set to a region R12 being a region other than the region R11 in the first slice. Since the second weighting coefficient is larger than the first weighting coefficient, a synthetic image can be obtained in which the periphery of the femoral head is emphasized to be easily recognized.

Similarly, as illustrated in FIG. 16, in the second slice, the second weighting coefficient is set to a predetermined region R21 including the second coordinates of the upper-end center CTL2 of the sacrum, and the first weighting coefficient is set to a region R22 being a region other than the region R21 in the second slice. Since the second weighting coefficient is larger than the first weighting coefficient, a synthetic image can be obtained in which the periphery of the sacrum centrum is emphasized to be easily recognized.

For example, in the processing of generating the synthetic image in this embodiment, the synthetic image is generated with a first weighting coefficient of 0.5 set to the region R12 in the image of the first slice and a first weighting coefficient of 0.5 set to the region R22 in the image of the second slice, while a second weighting coefficient of 0.7 is set to the predetermined region R11 including the first coordinates on the first slice and a second weighting coefficient of 0.7 is set to the predetermined region R21 including the second coordinates on the second slice. This makes it possible to generate a synthetic image in which the vicinities of the first coordinates and the second coordinates are emphasized, thereby facilitating the diagnosis using the synthetic image.

Here, the predetermined region R11 including the first coordinates means a region in a predetermined range including the first coordinates set at Step S18 and can be defined, for example, as a range of coordinates (X−10, Y−10) to coordinates (X+10, Y+10). The size and shape of the predetermined region R11 are arbitrary and can be decided in consideration of the size and shape of the femoral head in this embodiment. These points are similar to the predetermined region R21 including the second coordinates, and the size and shape of the predetermined region R21 can be decided in consideration of the size and shape of the sacrum centrum. The region R11 and the region R21 do not always to have the same size and shape. For example, the region R11 may be set to be a square in consideration of the shape of the femoral head, and the region R21 may be set to be a rectangle in consideration of the shape of the sacrum.

Further, the unit of the region R11 and the region R21 to which the second weighting coefficient is set may be different from the unit of the coordinates set on the image of the slice. For example, the unit of the region R11 and the region R21 to which the second weighting coefficient is set may be set for each of four regions defined by 2×2 units of the coordinates set on the image of the slice. Furthermore, the unit of the predetermined region R11 including the first coordinates and the unit of the predetermined region R21 including the second coordinates may be the same or may be different.

Note that the setting of the second weighting coefficient in this embodiment may be performed to one of the predetermined region R11 including the first coordinates and the predetermined region R21 including the second coordinates. In other words, a second weighting coefficient larger than a first weighting coefficient only need to be set to at least one of the predetermined region R11 including the first coordinates and the predetermined region R21 including the second coordinates.

As described above, the X-ray diagnostic apparatus 1 according to this embodiment is configured to set, to the predetermined region R11 including the first coordinates and the predetermined region R21 including the second coordinates, the second weighting coefficient larger than the first weighting coefficient set to the other region R12 and region R22, and thus can emphasize the image near the femoral head at the first coordinates and emphasize the image near the sacrum centrum at the second coordinates at the time when generating the synthetic image. This enables generation of a synthetic image for further facilitating a diagnosis.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

For example, the data on the tomosynthesis image in each of the above embodiments is an example of the three-dimensional medical image data, and may be image data in another format such as an image by an X-ray CT. In other words, each of the above embodiments is applicable to image data as long as the image data is three-dimensional medical image data from which a plurality of slices can be cut out.

Besides, though the slice is designated based on the position of the femoral head and the position of the sacrum and the measured value being the geometric parameter is calculated to generate the auxiliary figure in each of the above embodiments, a slice may be designated based on another tissue such as another bone and internal organ of the subject P and a measured value being a geometric parameter may be calculated to generate an auxiliary figure. In short, the diagnostic image generation processing executed in the X-ray diagnostic apparatus 1 according to this embodiment is applicable to every tissue of the subject P.

In other words, although the diagnostic image generation processing executed in the X-ray diagnostic apparatus 1 is explained by taking a case where the evaluation target is the pelvis distortion as an example in each of the above embodiments, the evaluation target is not limited to the pelvis distortion. For example, the evaluation target can be a skeleton distortion, pelvis shape, or skeleton shape. Furthermore, the evaluation target can be an element other than bones.

Furthermore, the subject P in each of the above embodiments is not limited to the human being but may be an animal. For example, the diagnostic image generation processing is applicable to a case of making a diagnosis similar to the above diagnosis for the human being, for a monkey, and a case of evaluating the deformation of the spine of a dog or a cat and diagnosing a risk of osteoarthritis of the spine by the X-ray diagnostic apparatus or the like.

Besides, the image processing apparatus 40 composed of the processing circuitry 24, the display 30, the input circuit 32, and the storage circuit 34 is described as a part of the components of the X-ray diagnostic apparatus 1 in each of the above embodiments, but the image processing apparatus 40 is not always to be a part of the components of the X-ray diagnostic apparatus 1. For example, the image processing apparatus 40 may be composed of a work station or a personal computer so that the data on the tomosynthesis image is stored in an auxiliary storage such as a hard disk drive of the work station or the personal computer. In this case, the work station or the personal computer reads the data on the tomosynthesis image from the auxiliary storage and executes the above diagnostic image generation processing.

Furthermore, although the calculated geometric parameter and the generated superimposed image are displayed together on the display 30 in each of the above embodiments, it is possible to display the geometric parameter on the display 30 without displaying the superimposed image.

Figure 17:
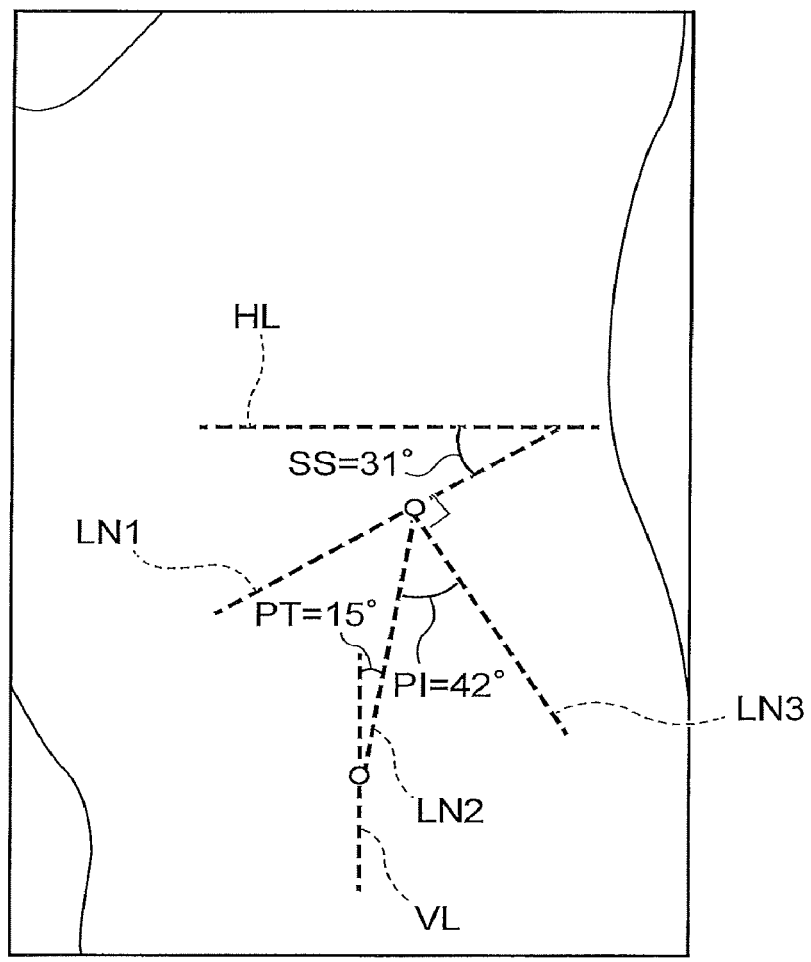
FIG. 17 is a view illustrating a modified example to display an auxiliary figure and a geometric parameter together on the display.
Figure 18:
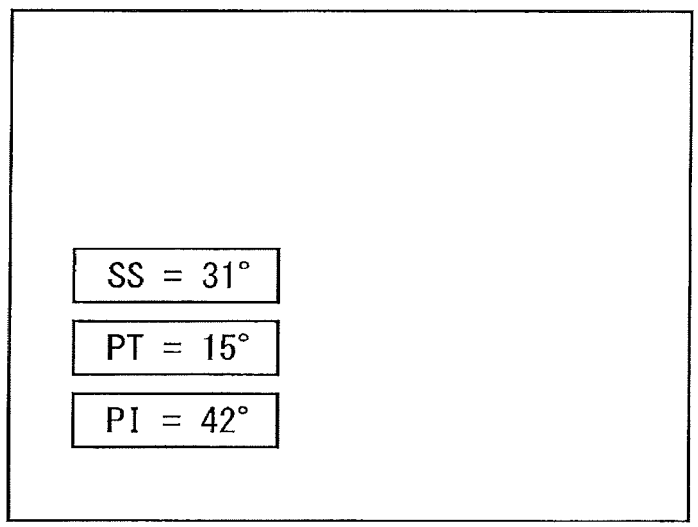
FIG. 18 is a view illustrating another modified example to display a geometric parameter without displaying the superimposed image.

For example, as shown in FIG. 17 corresponding to FIG. 10 in the first embodiment, it is possible to display the generated auxiliary figure and the calculated geometric parameter together on the display 30 without displaying the superimposed image. Also, as shown in FIG. 18, it is possible to display the geometric parameter on the display 30 just for information without displaying the auxiliary figure or the synthetic image.

In addition, it is possible to display the synthetic image and the geometric parameter on the display 30 without superimposing the auxiliary figure on the synthetic image. That is, it is optional to superimpose the auxiliary figure on the synthetic image. It is also optional how to display the geometric parameter on the display 30. For example, the geometric parameter can be displayed on the synthetic image, or the geometric parameter can be arranged on the display 30 so as not to overlap each other.

The invention claimed is:

1. An image processing apparatus comprising:
   processing circuitry configured to
   acquire three-dimensional medical image data;
   set coordinates of at least two or more elements to evaluate an evaluation target represented by the three-dimensional medical image data, on images of different positioning slices of the three-dimensional medical image data;
   calculate a measured value for evaluating the evaluation target based on the coordinates; and
   control a display to display the measured value;
   select at least two images from the images of the slices based on the coordinates and generate a two-dimensional synthetic image in which the selected images are synthesized,
   generate an auxiliary figure representing the measured value and generate a superimposed image in which the auxiliary figure is superimposed on the synthetic image, and
   control the display to display the superimposed image.

2. The image processing apparatus according to claim 1, wherein the processing circuitry is configured to select the images of the slices on which the coordinates are set and generate the synthetic image by synthesizing the selected images.

3. The image processing apparatus according to claim 2, wherein the processing circuitry is configured to generate the synthetic image by averaging pixel values of the selected images.

4. The image processing apparatus according to claim 1, wherein the processing circuitry is configured to select images of a plurality of slices including each of the slices on which the coordinates are set and at least one slice near said each of the slices and generate the synthetic image by synthesizing the selected images.

5. The image processing apparatus according to claim 4, wherein the processing circuitry is configured to generate the synthetic image by setting a weighting coefficient to the selected images of the slices and by weighting-averaging the images of the slices based on the weighting coefficient.

6. An image processing apparatus comprising:
   processing circuitry configured to
   acquire three-dimensional medical image data;
   set coordinates of at least two or more elements to evaluate an evaluation target represented by the three-dimensional medical image data, on images of different positioning slices of the three-dimensional medical image data;

calculate a measured value for evaluating the evaluation target based on the coordinates; and
control a display to display the measured value;
set first coordinates on an image of a first slice including a first element of the two or more elements, and set second coordinates on an image of a second slice including a second element of the two or more elements; and
generate the two-dimensional synthetic image based on the three-dimensional medical image data in a region including the first slice and the second slice;
generate an auxiliary figure based on the first coordinates and the second coordinates and generate a superimposed image in which the auxiliary figure is superimposed on the synthetic image, and
control the display to display the superimposed image.

7. An image processing apparatus comprising:
processing circuitry configured to
acquire three-dimensional medical image data;
set coordinates of at least two or more elements to evaluate an evaluation target represented by the three-dimensional medical image data, on images of different positioning slices of the three-dimensional medical image data;
calculate a measured value for evaluating the evaluation target based on the coordinates; and
control a display to display the measured value;
set first coordinates on an image of a first slice including a first element of the two or more elements, and set second coordinates on an image of a second slice including a second element of the two or more elements; and
generate the two-dimensional synthetic image based on the three-dimensional medical image data in a region including the first slice and the second slice;
set third coordinates on an image of a third slice including a third element of the two or more elements; and
generate the synthetic image based on the three-dimensional medical image data in a region including the first slice, the second slice, and the third slice.

8. The image processing apparatus according to claim 6, wherein the processing circuitry is configured to
calculate at least two average values of the first coordinates, the second coordinates, and the third coordinates,
generate an auxiliary figure using the average values, and
generate the superimposed image in which the auxiliary figure is superimposed on the synthetic image.

9. An image processing apparatus comprising:
processing circuitry configured to
acquire three-dimensional medical image data;
set coordinates of at least two or more elements to evaluate an evaluation target represented by the three-dimensional medical image data, on images of different positioning slices of the three-dimensional medical image data;
calculate a measured value for evaluating the evaluation target based on the coordinates; and
control a display to display the measured value;
set first coordinates on an image of a first slice including a first element of the two or more elements, and set second coordinates on an image of a second slice including a second element of the two or more elements; and
generate the two-dimensional synthetic image based on the three-dimensional medical image data in a region including the first slice and the second slice;
generate the synthetic image by setting a weighting coefficient to at least one of a region including the first coordinates on the first slice and a region including the second coordinates on the second slice, and by weighting-averaging the image of the first slice and the image of the second slice based on the weighting coefficient for the region to which the weighting coefficient is set.

10. The image processing apparatus according to claim 6, wherein the processing circuitry is configured to control the display to display the superimposed image and the measured value together.

11. The image processing apparatus according to claim 6, wherein the processing circuitry is configured to
calculate a first auxiliary line linking the first coordinates on the image of the first slice and the second coordinates on the image of the second slice; and
generate the superimposed image by superimposing the first auxiliary line as the auxiliary figure on the synthetic image.

12. The image processing apparatus according to claim 6, wherein the processing circuitry is configured to
calculate an angle between the first auxiliary line and a vertical line intersecting the first auxiliary line;
generate the superimposed image by further superimposing the vertical line as the auxiliary figure on the synthetic image; and
control the display to display the angle between the first auxiliary line and the vertical line together with the superimposed image.

13. The image processing apparatus according to claim 6, wherein the processing circuitry is configured to
calculate a line of a sacrum centrum based on the second coordinates on the image of the second slice; and
generate the superimposed image by further superimposing the line of the sacrum centrum and a horizontal line intersecting the line of the sacrum centrum as the auxiliary figure on the synthetic image.

14. The image processing apparatus according to claim 13, wherein the processing circuitry is configured to
calculate an angle between the line of the sacrum centrum and the horizontal line; and
control the display to further display the angle between the line of the sacrum centrum and the horizontal line together with the superimposed image.

15. The image processing apparatus according to claim 13, wherein the processing circuitry is configured to
calculate a second auxiliary line vertical to the line of the sacrum centrum and an angle between the first auxiliary line and the second auxiliary line;
generate the superimposed image by further superimposing the second auxiliary line as the auxiliary figure on the synthetic image; and
control the display to further display the angle between the first auxiliary line and the second auxiliary line together with the superimposed image.

16. An image processing apparatus comprising:
processing circuitry configured to
acquire three-dimensional medical image data;
set coordinates of at least two or more elements to evaluate an evaluation target represented by the three-dimensional medical image data, on images of different positioning slices of the three-dimensional medical image data;
calculate a measured value for evaluating the evaluation target based on the coordinates; and
control a display to display the measured value;

set first coordinates on an image of a first slice including a first element of the two or more elements, and set second coordinates on an image of a second slice including a second element of the two or more elements; and
generate the two-dimensional synthetic image based on the three-dimensional medical image data in a region including the first slice and the second slice;
set a center of a femoral head as the first coordinates and set a center of a sacrum centrum as the second coordinates by image analysis.

\* \* \* \* \*